United States Patent [19]

Mitchell

[11] Patent Number: 5,558,634
[45] Date of Patent: Sep. 24, 1996

[54] APPARATUS FOR THE REMOVAL OF ADHERENT VISCOELASTIC

[76] Inventor: Paul G. Mitchell, 822 Pinnacle Pl., Marietta, Ga. 30062

[21] Appl. No.: 265,762

[22] Filed: Jun. 27, 1994

Related U.S. Application Data

[63] Continuation of Ser. No. 56,373, Apr. 30, 1993, Pat. No. 5,358,473.

[51] Int. Cl.⁶ ........................................... A61M 1/00
[52] U.S. Cl. ................... 604/35; 604/43; 604/27; 606/107
[58] Field of Search ................... 604/22, 27, 28, 604/35, 43–45; 606/107

[56] References Cited

U.S. PATENT DOCUMENTS

| | | | |
|---|---|---|---|
| 3,930,505 | 1/1976 | Wallach. | |
| 4,851,513 | 7/1989 | Devore et al. | |
| 4,897,079 | 1/1990 | Zaleski et al. | 604/22 |
| 4,904,238 | 2/1990 | Williams | 604/43 |
| 4,935,006 | 6/1990 | Hasson | 604/43 |
| 5,084,013 | 1/1992 | Takase | 604/43 |
| 5,395,315 | 3/1995 | Griep | 604/35 |

*Primary Examiner*—Randall L. Green
*Assistant Examiner*—Ronald K. Stright, Jr.
*Attorney, Agent, or Firm*—Walter A. Hackler

[57] ABSTRACT

A method and apparatus is disclosed for the removal of viscoelastic material from an eye chamber. The apparatus enables a procedure, or method, which includes the steps of directing an irrigation fluid toward a viscoelastic material disposed in an eye chamber in order to loosen said viscoelastic material from eye chamber surfaces, hydraulically forcing the loosened viscoelastic material from the chamber surfaces, and aspirating the loosened viscoelastic material from the eye chamber.

10 Claims, 2 Drawing Sheets

5,558,634

APPARATUS FOR THE REMOVAL OF ADHERENT VISCOELASTIC

This is a continuation of prior U.S. patent application Ser. No. 08/056,373, filed on Apr. 30, 1993, now U.S. Pat. No. 5,358,473.

The present invention generally relates to surgical instruments and more particularly to needle apparatus and a method for removal of viscoelastic material from an eye chamber.

In many ophthalmic surgical procedures such as, for example, intraocular lens implantation, cataract surgery and retinal detachment repair, a viscous gel-like composition is utilized to fill the chambers of the eye in order to protect sensitive tissue, in particular the cornea endothelium from trauma.

While many compositions have been utilized, commonly employed compositions include solutions of hyaluronic acid, chondroitin sulfate and methylcellulose. The many various viscoelastic materials heretofore used for this purpose may be classified as either adhesive viscoelastic, such as Viscoat®, or cohesive viscoelastic, such as Healon®.

Adhesive viscoelastic materials are effective in coating the endothelium well and further resist washout during phaco surgery, which includes the irrigation of the eye chamber with balanced saline solution (BSS).

Unfortunately, adhesive viscoelastic materials are difficult to remove because, while being adhesive, they are not cohesive, that is, they do not intend to hold together, but preferentially, adhere to eye surfaces. This is particularly troublesome in conventional eye surgery in which the viscoelastic material is aspirated at completion of surgery.

Such aspiration is required because retained viscoelastic material causes elevated intraocular pressure. Unless a complete removal of the viscoelastic material at the end of the operation is effected, post operative intraocular pressure may be increased.

As briefly hereinabove mentioned, a desirable viscoelastic material for eye surgery, including phacoemulsification, sticks, or adheres, to the tissues in the eye with greater adherence than it sticks to itself. Thus, it is not easily dislodged by turbulence. This is of particular importance when the adhesive viscoelastic material must be removed from areas such as anterior chamber angle, sulcus and the capsular bag behind the intraocular lens which are not easily accessible to current instrumentation. Thus, it is apparent that the same adhesive property that provides the best coating for endothelium during surgery also makes it difficult to remove the material at the end of the operation.

Alternative materials, which may be classified as cohesive, viscoelastic materials, such as Healon, hereinabove noted, are easily aspirated or irrigated out enmass since they adhere, or stick, to themselves. (Cohesive property). Unfortunately, such cohesive viscoelastic materials are not preferred by surgeons because they do not adhere to the sensitive tissue, to be protected, as well as the adhesive viscoelastic materials.

Heretofore utilized irrigation/aspiration instruments for use in eye surgery have utilized needles suitable for singly irrigating, and aspirating the eye chamber. The heretofore irrigation has been performed using a gradual flow of BSS for the sole purpose of replacing the fluids being pumped out or leaking out of the eye chamber.

The apparatus and method of the present invention enables a use of the preferred adhesive viscoelastic materials in ophthalmic surgery procedures.

SUMMARY OF THE INVENTION

The method in accordance with the present invention for the removal of viscoelastic material from the eye chamber, generally includes the steps of directing an irrigation fluid toward a viscoelastic material disposed in an eye chamber in order to loosen the viscoelastic material from chamber surfaces. This step provides a gentle jet of fluid irrigation to sweep adhesive viscoelastic material off surfaces.

Secondly, in accordance with the method of the present invention, the loosened viscoelastic material is hydraulically forced from the chamber surfaces, in particular, narrow spaces in the anterior chamber. Thereafter, the loosened viscoelastic material is aspirated from the eye chamber.

In accordance with the method of the present invention, the steps of directing an irrigation fluid and aspirating the loosened viscoelastic material may be performed simultaneously. This must be contrasted with a prior art procedures and apparatus which are designed for separately irrigating the eye chamber and sequentially aspirating viscoelastic material therefrom.

The method of the present invention is particularly advantageous since adhesive viscoelastic material cannot be easily pulled, or aspirated, out of many narrow areas in the eye chamber. Further continued asperation in accordance with the prior art merely removes the irrigation fluid.

Thus, the present invention provides a continuous sweep of fluid with controlled removal of a volume of loosened material from an eye chamber.

More particularly, a method in accordance with the present invention comprises the step of circulating the loosened viscoelastic material from the eye surface to an aspiration port with the irrigation fluid.

Preferably, the irrigation fluid is directed toward the viscoelastic materials in the form of a jet. This must be contrasted with the prior art devices which only provide a diffused introduction of irrigation fluid into an eye chamber for the purpose of maintaining eye chamber pressure and for flushing fragmented crystaline lens for example, from the eye chamber.

More specifically, a plurality of irrigation fluid jets may be provided for loosening and circulating viscoelastic material from surfaces on the eye chamber and the loosened viscoelastic material is aspirated leeward from the directed irrigation fluid.

The apparatus in accordance with the present invention generally includes means for directing an irrigation toward a viscoelastic material disposed in an eye chamber in order to loosen the viscoelastic material from the eye surface and hydraulically forcing the loosened viscoelastic material from the chamber surfaces along with means for aspirating the loosened viscoelastic material from the eye chamber.

More particularly, the apparatus in accordance with the present invention, includes a needle having means defining a first lumen therein for accepting irrigation fluid and means defining a first irrigation port in the needle, for emitting the irrigation fluid from the first lumen at a first angle to a longitudinal needle axis. A second irrigation port may be provided in the needle for emitting of the irrigation fluid from the first lumen at a second angle to the needle axis. The emission of irrigation fluid from the first and second irrigation ports may be in a single plane which is perpendicular to the needle axis.

Means may be provided which define a second lumen in the needle for aspirating the loosened viscoelastic material and irrigation fluid, which includes an aspiration port in fluid communication with the second means for receiving the loosened viscoelastic material at a third angle to the needle axis.

In one embodiment of the present invention, the first and second lumens are disposed in a parallel relationship, while in another embodiment of the invention, the first and the second lumens are coaxially disposed within the needle.

The apparatus of the present invention further includes, in combination, an adhesive viscoelastic material and a needle which includes means for directing an irrigation fluid toward the viscoelastic material disposed on an eye chamber surface in order to loosen the viscoelastic material and hydraulically force the loosened viscoelastic material from the eye chamber surface along with a means for aspirating the viscoelastic material from the eye chamber.

In addition, the method of the present invention is useful in ophthalmic surgery includes the steps of coating sensitive eye tissue in an eye chamber with an adhesive viscoelastic material and thereafter directing an irrigation fluid toward the viscoelastic material in order to loosen the viscoelastic material from the sensitive eye tissues and hydraulically force the loosened viscoelastic material from the sensitive eye tissues and aspirating the loosened viscoelastic material from the eye chamber.

BRIEF DESCRIPTION OF THE DRAWINGS

The advantages and features of the present invention will appear from the following description, when considered in conjunction with the accompanying drawings in which.

DETAILED DESCRIPTION

Figure 1:
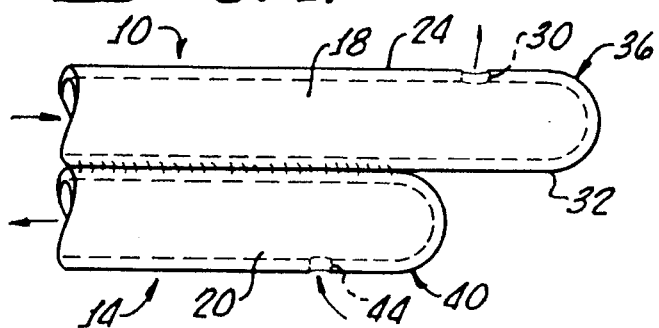
FIG. 1 is a cross-sectional view of apparatus in accordance with the present invention, suitable for carrying out the method of the present invention.

Turning now to FIG. 1, there is generally shown apparatus 10 in accordance with the present invention for the removal of viscoelastic material from an eye chamber, which specifically includes a needle 14 including an irrigation lumen 18 therein and an aspiration lumen 20 therein.

Only a tip portion 24, the needle 14 is shown, the tip portion 24 being coupled in a conventional manner with a conventional irrigation/aspiration handpiece providing irrigation fluid to the irrigation lumen 18 and the suction to the aspiration lumen 20. The conventional phaco handpiece and coupling device for securing the needle 14 thereto are not part of the present invention and therefore not shown for the sake of clarity.

An irrigation port 30 is disposed in a portion 32 of the irrigation side 36 of the needle 14 protruding past an aspiration side 40 of the needle 14. An opposing aspiration port 44 is disposed in the aspiration side 40 of the needle 14 facing in opposing direction to the irrigation port 30. The operation of this device will be hereinafter described in greater detail.

Figure 1A:
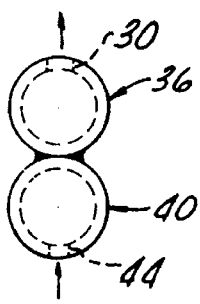
FIG. 1A is a cross-sectional end view of the embodiment shown in FIG. 1.
Figure 2:
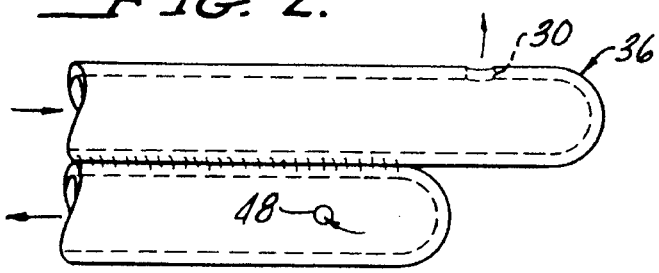
FIG. 2 is a cross-sectional view of a second embodiment of the present invention utilizing one irrigation port and two aspiration ports.
Figure 2A:
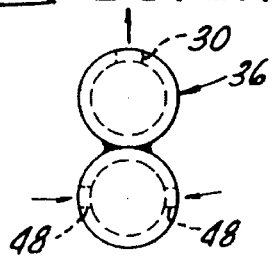
FIG. 2A is an end view of the embodiment shown in FIG. 2.

FIG. 1A is an end view of the embodiment shown in FIG. 1, FIGS. 2 and 2A are views of an alternative embodiment similar in all respects to the needle 14 as shown in FIG. 1, except that two opposing aspiration ports 48, are utilized.

Figure 3:
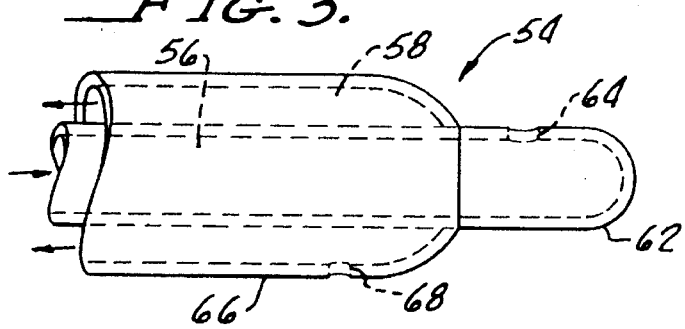
FIG. 3 is an alternative embodiment of the present invention showing coaxial lumens.
Figure 3A:
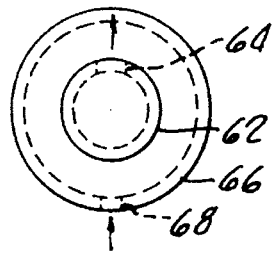
FIG. 3A is an end cross-sectional view of the embodiment shown in FIG. 3.

Alternative embodiments of the present invention are shown in FIGS. 3, 3A, 4 and 4A. FIG. 3 shows a needle 54 having coaxial irrigation lumen 56 and aspiration lumen 58 and extended tip 62 communicating with the irrigation lumen 56 includes an irrigation port 64 and an outer sleeve 66 includes an aspiration port 68 communicating with the aspiration lumen 58. As shown in both FIGS. 3 and 3A, the aspiration port 68 and irrigation port 64 face in opposite directions and the operation thereof will be hereinafter described in greater detail.

Figure 4:
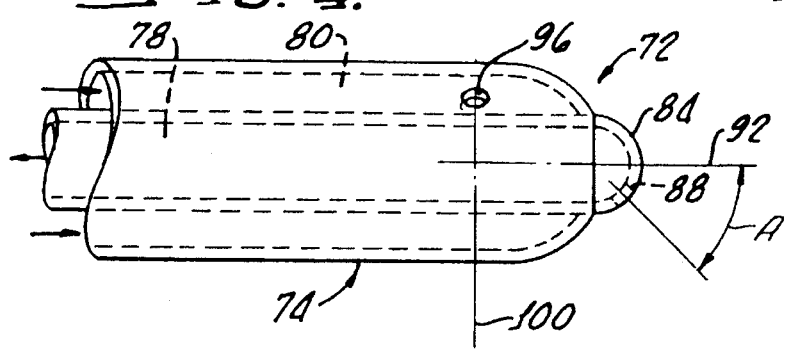
FIG. 4 is yet another alternative embodiment of the present invention.
Figure 4A:
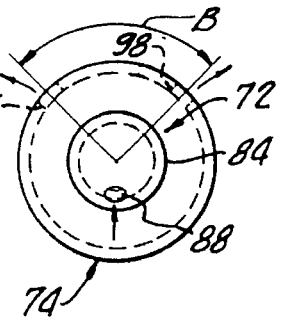
FIG. 4A is an end view of the embodiment shown in FIG. 4.

Turning now to FIG. 4, there is yet another embodiment 72 of a needle 74 in accordance with the present invention, having an inner aspiration lumen 78 and an outer irrigation lumen 80 in a coaxial relationship. In this embodiment, a tip 84 protrudes from the needle 74 and includes an aspiration port 88 in fluid communication with the aspiration lumen 78. In this instance, the port 88 is disposed in the tip of 84 at a position so that the aspiration of fluids into the aspiration lumen 78 occurs at an acute angle A to a longitudinal axis 92 with the needle 74. As best shown in FIG. 4A, two irrigation lumen ports 96, 98 are provided in line for emitting irrigation fluid in a plane 100, which may be perpendicular to the longitudinal axis 92.

As also shown in FIG. 4a, the aspiration port 88 may be disposed about 135 degrees from each irrigation ports 96, 98.

In operation, the plurality of the irrigation ports 96, 98 disposed at approximately 90 degrees from one another, enables manual rotation of the needle 74 to provide a greater degree of access to narrow or relatively remote portions of the eye chamber for the flushing of adherent vasoelastic material thereoutof. That is, a rotation of 45 degrees as shown by the double headed arrow B in FIG. 4A enables irrigation from the Ports 96, 98 to be directed over a 180 degree range.

In order to provide a proper supply of irrigation fluid which is directed from the needle 74, the irrigation ports may be between about 0.3 and about 0.5 mm diameter. It has also been found that an aspiration port diameter in the range of about 0.2 to about 0.3 mm is sufficient for aspirating fluid and loosened adherent viscoelastic material from the eye chamber.

The advantages of the hereinabove described apparatus and description of the method in accordance with the present invention may be more appreciated when taken in consideration of the representation shown in FIGS. 5 and 6.

Figure 5:
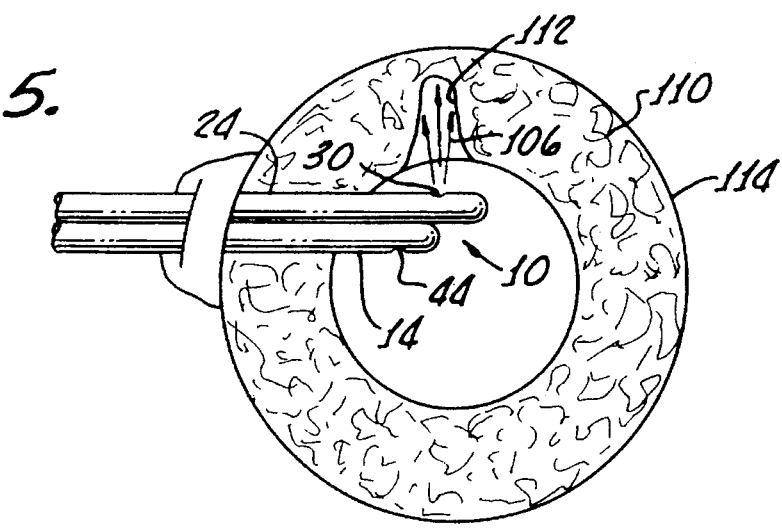
FIGS. 5 and 6 are representations of the method of the present invention showing the loosening of a viscoelastic material by irrigation fluid, hydraulic forcing of the loosened vascular material from chamber surfaces and aspiration thereof from the eye chamber.
Figure 6:
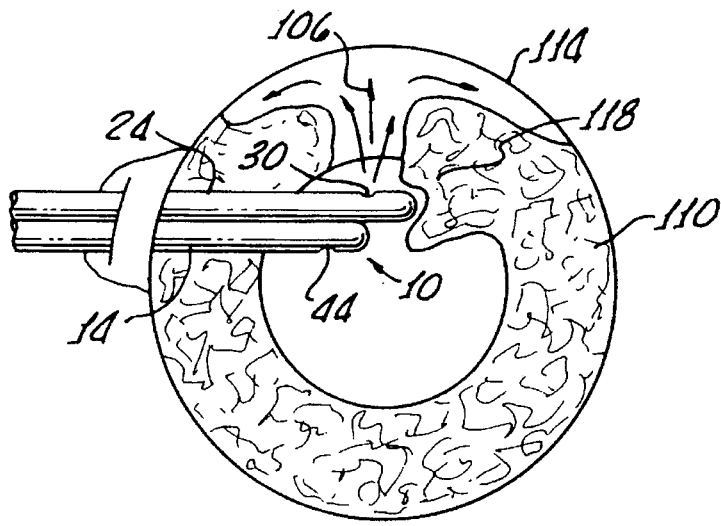

In FIG. 5, the needle 14 is shown inserted into an eye chamber and an irrigation of fluid is directed toward adherent viscoelastic material 110 in the form of a gentle jet 106 which causes penetration 112 by the irrigation fluid which, after continued irrigation, as shown in FIG. 6, the jet 106 lifts the adherent viscoelastic material 110 from an eye chamber surface 114 and hydraulically forces the loosened material 118, causing breakup thereof, so that it may be aspirated by the port 44 leeward from the jet 106. That is, in a direction opposite or away from the direction of the jet 106.

While the embodiment of the present invention shown in FIG. 1 is illustrated in FIGS. 5 and 6, any of the other embodiments of the present invention may be utilized and the operation thereof consistent with the presentation shown in FIGS. 5 and 6.

Figure 7:
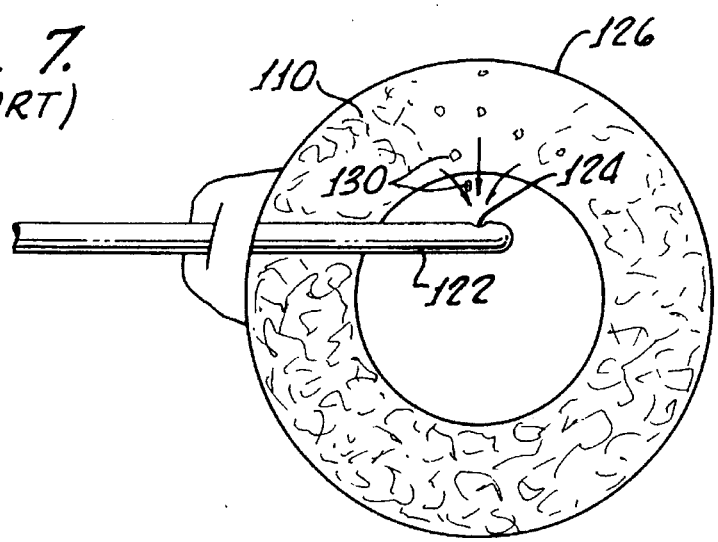
FIG. 7 is a representation of the prior art utilizing aspiration only for the removal of adherent viscoelastic material.

The apparatus method of the present invention must be contrasted with that of the prior art as shown in FIG. 7. A needle 122 therein having one or more lumen therein are utilized for irrigation and aspiration. One or more ports 124 provide a diffuse irrigation stream not suitable for hydraulically loosening and forcing loosened viscoelastic from an eye chamber surface 126, as is the case with the present invention.

As hereinbefore pointed out, the adherent nature of preferred viscoelastic material inhibits the removal thereof of eye surfaces 126. Therefore, the diffuse irrigation provided by the prior art does not adequately remove the adhesive viscoelastic material.

As shown during aspiration of the material 110, it breaks into smaller pieces 130 in the immediate vicinity of the needle 122, since the material 110 adheres to surfaces 126 more than it does to itself Thus, in the prior art device, an attempt to aspirate, or pull, the material 110 from the surface, inevitably results in removal of only the adjacent material 110, which necessitates the scavenging of all interior surfaces to obtain total removal of the viscoelastic material 110. This necessitates an unnecessarily long and hazardous procedure in order to remove all of the viscoelastic elastic material 110 from the area such as the anterior chamber angle, ciliary sulcus and the capsular bag behind the intraocular lens.

The present invention, as illustrated in FIGS. 5 and 6, facilitates the removal of the viscoelastic material 110 by sweeping the material 110 off surfaces 114 and hydraulically forcing it out of the narrow spaces into the anterior chamber where the loosened material 118 is easily aspirated. That is, in effect, the viscoelastic material 110 is pushed from the surfaces 114 rather than being sucked, or aspirated therefrom, as has been the case with prior art apparatus and procedures.

Although there has been hereinabove described apparatus and method for the removal of viscoelastic material from an eye chamber in accordance with the present invention, for the purpose of illustrating the manner in which the invention may be used to advantage, it should be appreciated that the invention is not limited thereto. Accordingly, any and all modification, variations, or equivalent arrangements which may occur to those skilled in the art should be considered to be within the scope of the present invention as defined in the appended claims.

What is claimed is:

1. Apparatus for the removal of viscoelastic material from an eye chamber, said apparatus comprising:

first irrigation port means for directing a jet fluid toward a viscoelastic material disposed in an eye chamber to first penetrate said viscoelastic material and thereafter loosen said viscoelastic material from the chamber surfaces without substantial breakup of the viscoelastic material and hydraulically forcing by pushing the loosened viscoelastic material from the eye chamber surfaces without substantial breakup of the viscoelastic material, said first irrigation port means comprising an opening having a diameter of between about 0.3 mm and about 0.5 mm; and aspiration port means for aspirating the loosened viscoelastic material from the eye chamber.

2. The apparatus according to claim 1 further comprising a needle having first lumen means, in fluid communication with said irrigation port means, for accepting said irrigation fluid, said first irrigation port means being disposed in said needle at a position for emitting the jet of irrigation fluid from said first lumen means at a first angle to a longitudinal needle axis.

3. The apparatus according to claim 2 further comprising second irrigation port means, disposed in said needle, for emitting a second jet of irrigation fluid from said first lumen means at a second angle to the needle axis.

4. The apparatus according to claim 3 wherein the first and second irrigation port means are aligned for emitting irrigation fluid on a plane.

5. The apparatus according to claim 4 wherein said plane is perpendicular to the needle axis.

6. The apparatus according to claim 5, wherein the aspiration port means comprises an aspirating port and a second lumen, said aspiration port being disposed at a third angle to the needle axis.

7. The apparatus according to claim 6 wherein said first and second lumen means are coaxially disposed within said needle.

8. The apparatus according to claim 7 wherein the first and second irrigation port means are disposed at about 90 angular degrees from one another.

9. The apparatus according to claim 8 wherein said aspirating port means is disposed at about 135 angular degrees from each of the irrigating port means.

10. The apparatus according to claim 6 wherein said first and second lumen means are disposed in a parallel relationship within said needle.

\* \* \* \* \*